United States Patent
Mungcal

(10) Patent No.: US 6,666,683 B2
(45) Date of Patent: Dec. 23, 2003

(54) DENTAL RING HAVING ORTHOGONAL PROTUBERANCE

(76) Inventor: Don Mungcal, 255 S. Grand Ave., Apt. #1403, Los Angeles, CA (US) 90012

( * ) Notice: Subject to any disclaimer, the term of this patent is extended or adjusted under 35 U.S.C. 154(b) by 89 days.

(21) Appl. No.: 10/043,674

(22) Filed: Jan. 9, 2002

(65) Prior Publication Data

US 2003/0129562 A1 Jul. 10, 2003

(51) Int. Cl.[7] .................................................. A61C 7/00
(52) U.S. Cl. ...................................................... 433/149
(58) Field of Search ................................ 433/149, 155, 433/39

(56) References Cited

U.S. PATENT DOCUMENTS

| | | | |
|---|---|---|---|
| 388,620 A | * | 8/1888 | Booth ........................... 433/39 |
| 440,509 A | | 11/1890 | Sawhill |
| 465,555 A | | 12/1891 | Cross et al. |
| 511,619 A | | 12/1893 | Ivory |
| 531,802 A | | 1/1895 | Libby |
| 545,754 A | | 9/1895 | Wishart |
| 2,311,141 A | | 2/1943 | True |
| 2,706,333 A | | 4/1955 | Schultz |
| 4,718,852 A | | 1/1988 | Galler |
| 5,607,302 A | | 3/1997 | Garrison et al. |
| 6,206,697 B1 | | 3/2001 | Hugo |
| 6,220,858 B1 | | 4/2001 | McKenna |
| 6,293,796 B1 | * | 9/2001 | Trom et al. .................. 433/155 |
| 6,325,625 B1 | * | 12/2001 | Meyer .......................... 433/139 |
| 2002/0155410 A1 | * | 10/2002 | Bills ............................ 433/153 |

FOREIGN PATENT DOCUMENTS

SU             141981        12/1960

* cited by examiner

*Primary Examiner*—John J. Wilson
(74) *Attorney, Agent, or Firm*—Lewis, Brisbois, Bisgaard & Smith LLP

(57) ABSTRACT

A dental ring for use in installing interproximal fillings in the teeth of human patients in a dental office. In its most fundamental embodiment, the dental ring exhibits a circular ring comprised of metal which includes a gap formed in the ring for defining a first terminal end and a second terminal end. A pair of downward extending parallel flanges includes a first parallel flange extending from the first terminal end and a second parallel flange extending from the second terminal end where the parallel flanges serve to separate a decayed tooth from an adjacent tooth. Finally, a protuberance is formed onto an interior surface of one of the parallel flanges for securing a matrix foil about the decayed tooth. In an alternative embodiment, a protuberance is formed onto an interior surface of each of the first and second parallel flanges for securing a matrix foil about the decayed tooth.

9 Claims, 4 Drawing Sheets

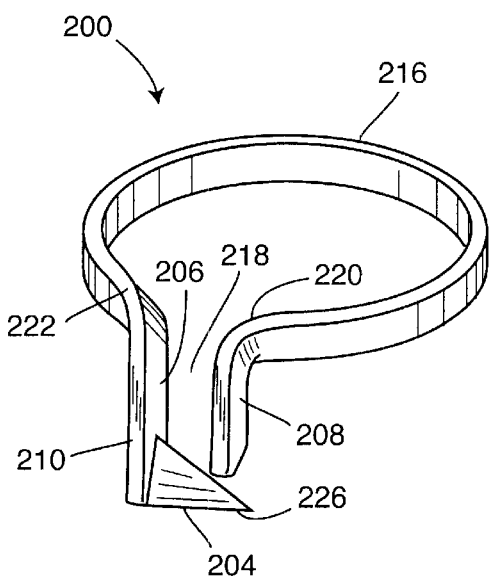
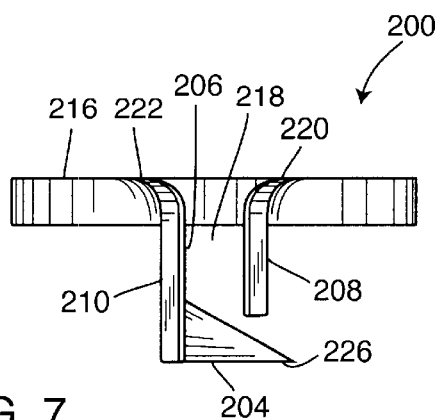
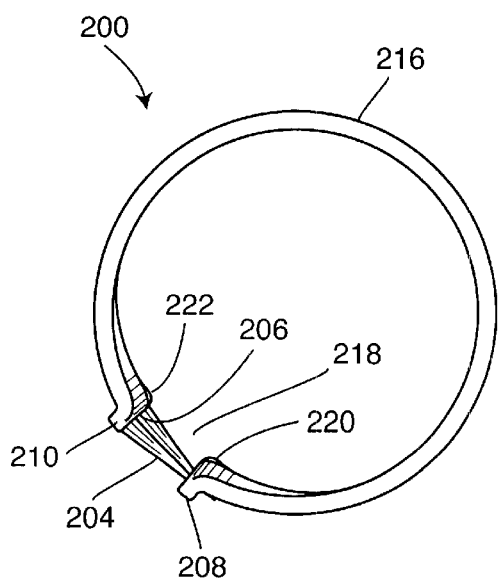
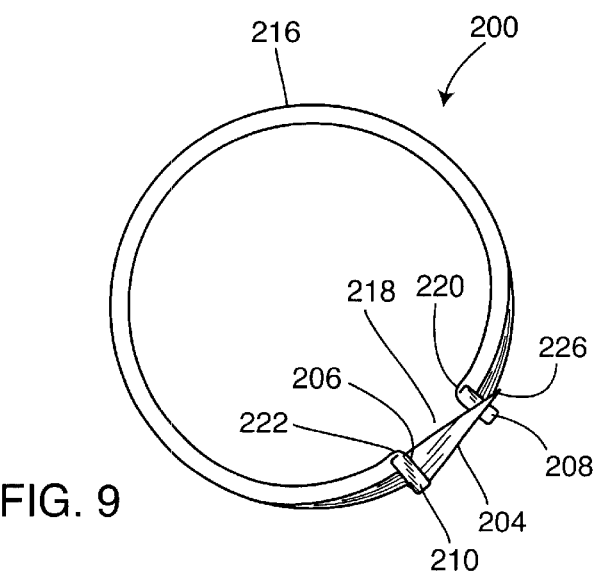
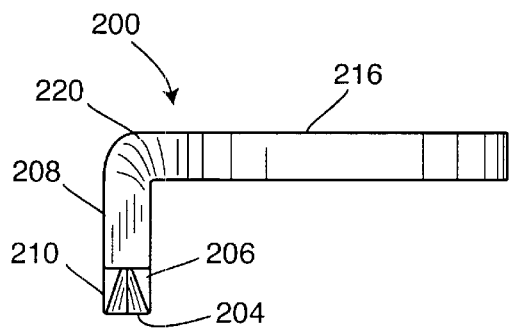

DENTAL RING HAVING ORTHOGONAL PROTUBERANCE

BACKGROUND OF THE INVENTION

1. Technical Field

The present invention relates to dental devices. More specifically, the present invention relates to methods and apparatus for a dental ring typically used in a dental office for installing interproximal fillings in the teeth of human patients, the dental ring having at least one orthogonal protuberance for securing a matrix foil about a decayed tooth.

2. Background Art

The prior art is directed to methods and apparatus for dental rings typically used in a dental office for installing interproximal fillings in human teeth.

A dental cavity can occur at the interface of two teeth where the cavity is actually in one or both of the teeth. This type of cavity is known as "interproximal" and the process in dentistry of filling this type of cavity in one or both teeth is identified as an "interproximal filling". The initial steps in addressing the cavity is to numb the relevant nerves and then to create a hole from the top of the tooth with an appropriate dental drilling device until all of the decay is removed. In order to fill the tooth with dental material to replace the decayed enamel that has been removed by drilling, three components were required in the prior art. Those components include (a) a matrix foil, (b) a small wooden wedge, and (c) one of a plurality of dental rings for use in interproximal fillings known in the prior art.

The matrix foil is a thin contoured piece of aluminum metal having a concave shape that is placed between the teeth, i.e., at the interface of two adjacent teeth, wherein at least one of those teeth is decayed. The matrix foil is positioned so that the decayed tooth of interest is captured (or partially surrounded) by the concave shape of the foil. The foil serves to (1) keep the filling material inserted into the decayed tooth from sticking to the adjacent tooth across the interface, and (2) to provide the new dental filling material with an interproximal shape so that after inserted and set, the filling material makes contact with, but does not stick to, the adjacent tooth. This contact feature is important in order to keep food particles from getting caught in the interface between the adjacent teeth which would increase the probability of further decay.

It is noted that a slight "gap" exists between the decayed tooth and the matrix foil once the matrix foil has been inserted at the interface between the two adjacent teeth. If just the matrix foil is positioned between the decayed tooth and the adjacent tooth, the gap, although slight, is too wide, i.e., the matrix foil does not fit snugly against the decayed tooth. Under these conditions, the dental tooth filling material will flow into the slight gap. A "ledge" comprised of the dental filling material is then created that extends into the interface of the adjacent teeth which interferes with proper flossing because the floss catches on the ledge and fails to clean the teeth. This situation creates a plaque trap which can result in further tooth decay. In the prior art, a "small wooden wedge" about the size of the end of a toothpick was positioned between the matrix foil and the tooth adjacent to the decayed tooth. Consequently, in the prior art, the wooden wedge was employed to force the matrix foil as close as possible to the decayed tooth or tooth being restored to close the slight "gap" between the decayed tooth and the matrix foil and to eliminate the possibility of forming a ledge.

The third component used in the prior art to fill a decayed tooth with dental filling material was one of a plurality of known "dental rings". A "dental ring" (typically known as a Palodent ring, Garrison ring, or Danville ring) was generally a metal ring having an interruption at one location along the perimeter thereof. The function of the prior art dental ring was to activate a slight separation between the two adjacent teeth (i.e., the decayed tooth and the tooth adjacent to the decayed tooth) to gain access to the filling site (which had already been drilled and prepared for filling), and to restore a contact between the two adjacent teeth. At the interruption or opening on the perimeter of the metal dental ring, a pair of parallel flanges were formed that were orthogonal (i.e., at right angles) to the plane of the dental ring.

Once the matrix foil and the small wooden wedge were positioned between the two adjacent teeth, the dental ring was inserted. Using a pair of manual forceps, the dental ring was forced open at the pair of parallel flanges increasing the inner diameter of the ring. The dental ring was then positioned around the tooth adjacent to the decayed tooth so that the parallel flanges of the dental ring forced the two adjacent teeth apart. The dental rings of the prior art were then anchored beneath the undercut of the adjacent tooth that the dental ring surrounds. The parallel flanges were positioned behind the matrix foil and forced the matrix foil around the decayed tooth. The drilling typically created a box shape for the purpose of receiving the dental filling material. The filling site was then prepared with the proper chemicals. The filling material was then added and hardened and could be overbuilt so that when the matrix foil and prior art dental ring were removed, there would be desirable contact between the restored tooth and the tooth adjacent to the restored tooth.

Some specific examples of the dental rings of the prior art include, for example, the Palodent dental ring. The Palodent dental ring is a heavy dental ring having flat parallel flanges located orthogonal to the plane of the dental ring at the interruption or opening in the ring. One of the problems with the Palodent dental ring is that it tends to pop-off or dislodge itself from the tooth to which it is attached and fall into the patients mouth. This situation creates an obvious hazard to the patient and to the other teeth in the patient's mouth. Another example of a prior art dental ring is the Garrison dental ring which exhibited a thinner, less robust construction having nail heads located at the end of the parallel flanges. The nail heads at the ends of the parallel flanges were intended to fit underneath the undercut of the tooth of interest for providing a more positive anchor. However, due to the less robust construction, the Garrison dental ring resulted in reduced structural strength.

A further example of a prior art dental ring was the Danville dental ring. The Danville dental ring included two flanges located at the interruption or opening in the plane of the dental ring. The two flanges were not parallel but converged in an effort to prevent the dental ring from popping off or dislodging from the tooth of interest. The ring construction was heavy duty and the converging flanges attempted to grasp the undercut of the tooth of interest. Unfortunately, dislodging of the dental ring continued to be a problem. A problem with all of the dental rings of the prior art was that there were too many component parts. The dental rings of the prior art were always positioned above the small wooden wedge located behind the matrix foil. Thus, the small wooden wedge caused the dental ring to dislodge and strike other teeth. Often it was difficult to position the small wooden wedge for maximum adaptation because the dental ring occupied too much space in and about the tooth to be restored. This problem resulted in an interproximal filling that included a ledge that interfered with flossing and created a plaque trap. Consequently, the small wooden wedge interfered with the proper operation of the prior art dental rings.

Thus, there is a need in the art for a dental ring for use in installing interproximal fillings in the teeth of human patients wherein the invention comprises an integral combination of a dental ring fashioned from heavy spring steel and including a pair of vertical flanges or legs orthogonal to the plane of the dental ring wherein at least one steel protuberance is mounted orthogonal to an interior face of at least one of the vertical flanges or legs for use in securing a matrix foil to the side of the tooth being restored.

DISCLOSURE OF THE INVENTION

Briefly, and in general terms, the present invention provides a new and improved dental ring having an orthogonal protuberance for use in a dental office for installing interproximal fillings in the teeth of human patients. The present invention provides an efficient means by which the dental ring including the orthogonal protuberance is employed for securing a matrix foil about a decayed tooth.

The present invention generally includes an integral combination of a dental ring fashioned from heavy spring steel which includes a pair of vertical flanges or legs orthogonal to the plane of the dental ring. In the present invention, at least one steel protuberance is mounted orthogonal to an interior surface of at least one of the vertical flanges or legs for use in securing a matrix foil to the side of the tooth being restored. This construction reduces the number of component parts associated with known dental rings. This is the case since one of the functions of the protuberance is the same as that of the small wooden wedge, i.e., employed in the past for adapting the matrix foil as close as possible to the tooth being restored. This design results in a more efficient and useful construction.

In a preferred embodiment, the dental ring having an orthogonal protuberance exhibits a construction of heavy spring steel having a pair of vertical flanges orthogonal to the plane of the dental ring. At least one of the pair of vertical flanges includes a protuberance that is orthogonal, i.e., at right angles, to the interior face or surface of the corresponding vertical flange. The protuberance which is formed on the dental ring is also typically fashioned from spring steel and can be wedge-shaped, cone-shaped, triangular-shaped, or semi-circular-shaped. In the preferred embodiment, the protuberance is illustrated as being wedge-shaped. The specific location at which the protuberance is formed on one or both of the vertical flanges is determined by the location of the cavity in and the structure of the patient's teeth, and the side of the patient's mouth in which the inventive dental ring is to be utilized.

The procedure utilized in restoring a decayed tooth when employing the dental ring of the present invention includes initially numbing the appropriate nerves in the area of the decayed tooth. Next, the decayed area is removed by utilizing an appropriate dental drilling device for creating a box shape receptacle for receiving dental filling material. The filling site is then prepared with the proper chemicals. Next, the concave matrix foil is positioned between the decayed tooth which is to be restored and an adjacent tooth. The inventive dental ring is then expanded with manual forceps and positioned around the adjacent tooth while the orthogonal protuberance is directed into the embrasure (i.e., triangular gap) between the adjacent tooth and the tooth to be restored. The protuberance forces the matrix foil against the tooth to be restored, closes any slight gap between the matrix foil and the tooth to be restored, assists the dental ring in grasping the undercut of the adjacent tooth upon which it is mounted, prevents the dental ring from popping off into the mouth of the patient, and eliminates the separate wooden wedge required in the prior art.

The present invention is generally directed to a dental ring having an orthogonal protuberance formed thereon for use in installing interproximal fillings in the teeth of human patients in a dental office. In its most fundamental embodiment, the dental ring for use in installing interproximal fillings in teeth exhibits a circular ring comprised of metal which includes a gap formed in the ring for defining a first terminal end and a second terminal end. A pair of downward extending parallel flanges includes a first parallel flange extending from the first terminal end and a second parallel flange extending from the second terminal end where the parallel flanges serve to separate a decayed tooth from an adjacent tooth. Finally, a protuberance is formed onto an interior surface of one of the parallel flanges for securing a matrix foil about the decayed tooth.

In an alternative embodiment, the inventive dental ring includes a circular ring comprised of metal which includes a gap formed in the ring for defining a first terminal end and a second terminal end. Also included is a pair of downward extending parallel flanges having a first parallel flange extending from the first terminal end and a second parallel flange extending from the second terminal end for separating a decayed tooth from an adjacent tooth. In addition, a first protuberance is formed onto an interior surface of the first parallel flange and a second protuberance is formed onto an interior surface of the second parallel flange where the first 1t protuberance and the second protuberance secure a matrix foil about the decayed tooth.

These and other objects and advantages of the present invention will become apparent from the following more detailed description, taken in conjunction with the accompanying drawings which illustrate the invention, by way of example.

BRIEF DESCRIPTION OF THE DRAWINGS

FIG. 6 is a perspective view of a first alternative embodiment of a dental ring of the present invention having a left side orthogonal protuberance showing a wedge protruding from a downward extending left side flange.

FIG. 7 is a front elevation of the dental ring of FIG. 6 showing a downward extending right side flange terminating above the wedge protruding from the downward extending left side flange.

FIG. 8 is a top plan view of the dental ring of FIG. 6 showing the downward extending right side flange blocking the view of the tip of the wedge of the orthogonal protuberance.

FIG. 9 is a bottom plan view of the dental ring of FIG. 6 showing the tip of the wedge beneath the downward extending right side flange.

FIG. 10 is a right side elevation of the dental ring of FIG. 6 showing the wedge protruding from the downward extending left side flange.

DETAILED DESCRIPTION OF THE INVENTION

Figure 1:
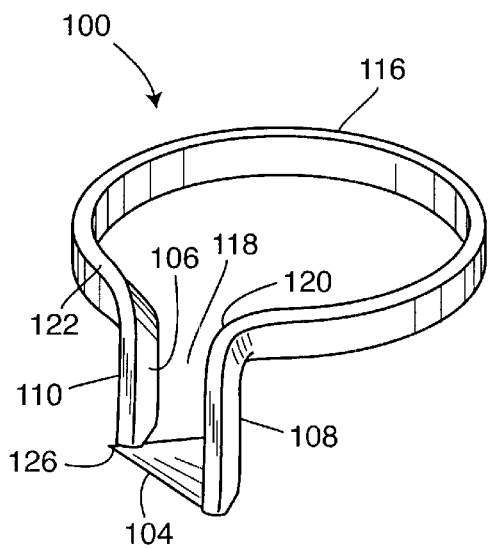
FIG. 1 is a perspective view of a dental ring of the preferred embodiment of the present invention having a right side orthogonal protuberance showing a wedge protruding from a downward extending right side flange.

The present invention is a dental ring 100 typically used in a dental office for installing interproximal fillings in the teeth 102 of human patients. The dental ring 100 includes a protuberance 104 orthogonally formed onto an interior surface 106 of one of a pair of downward extending parallel flanges 108, 110 for securing a matrix foil 112 about a decayed tooth 114. This construction is clearly exhibited as a dental ring 100 having a righted-handed protuberance 104 in FIGS. 1–5 and 16–17 and as a dental ring 200 of a first alternative embodiment shown in FIGS. 6–10.

Figure 2:
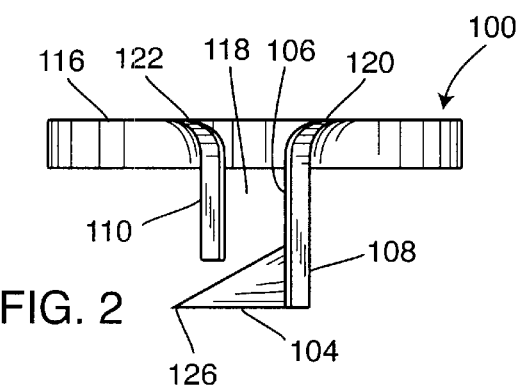
FIG. 2 is a front elevation of the dental ring of FIG. 1 showing a downward extending left side flange terminating above the wedge protruding from the downward extending right side flange.
Figure 3:
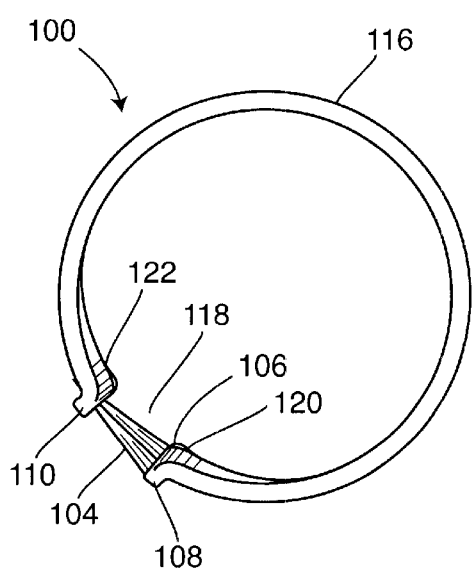
FIG. 3 is a top plan view of the dental ring of FIG. 1 showing the downward extending left side flange blocking the view of the tip of the wedge of the orthogonal protuberance.
Figure 4:
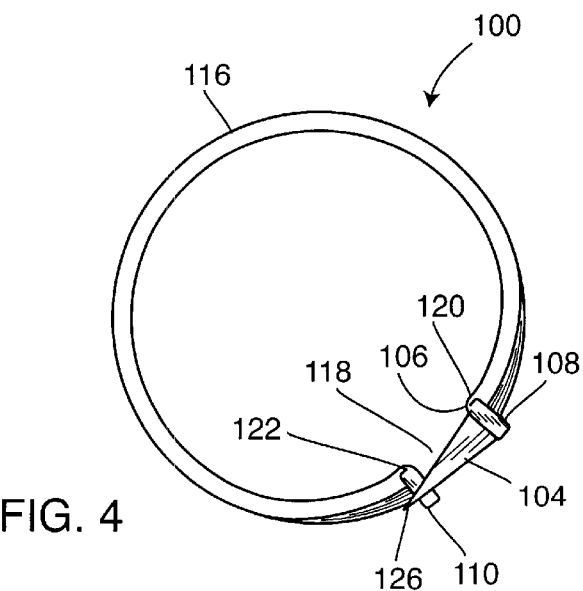
FIG. 4 is a bottom plan view of the dental ring of FIG. 1 showing the tip of the wedge beneath the downward extending left side flange.
Figure 5:
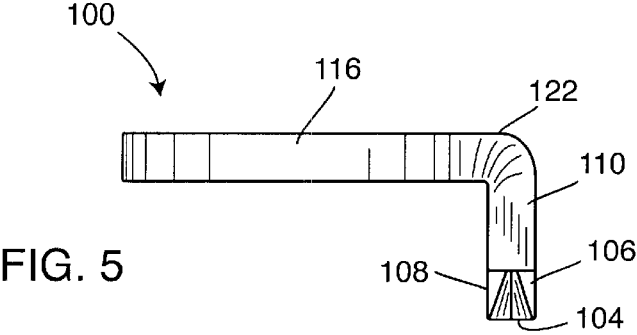
FIG. 5 is a left side elevation of the dental ring of FIG. 1 showing the wedge protruding from the downward extending right side flange.

We now turn our attention to the dental ring 100 which exhibits the right-handed protuberance 104 as is illustrated in FIGS. 1–5. The dental ring 100 includes a circular ring 116 comprised of heavy spring steel construction as shown in FIG. 1. The circular ring 116 lies in a single plane as is clearly shown in FIG. 2. The circular ring 116 is incomplete in that it contains a gap 118 formed in the circular ring 116. The gap 118 defines a first terminal end 120 and a second terminal end 122 of the circular ring 116 best shown in FIGS. 1 and 2. The pair of downward extending parallel flanges 108 and 110 are in mechanical communication with the circular ring 116. Extending downward from the first terminal end 120 of the circular ring 116 is the first parallel flange 108. Likewise, extending downward from the second terminal end 122 of the circular ring 116 is the second parallel flange 110. It is noted that the first parallel flange 108 and the second parallel flange 110 are each positioned orthogonal (i.e., at right angles) to the plane of the circular ring 116 as is best shown in FIG. 2.

Figure 16:
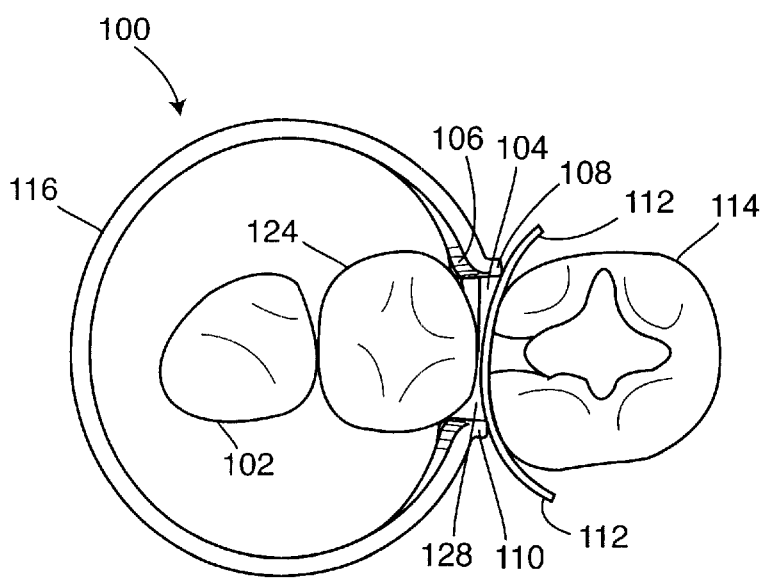
FIG. 16 is a top plan view of the dental ring of FIG. 1 shown installed for activating a slight separation between a tooth to be restored and a tooth adjacent to the tooth being restored.

The gap 118 in combination with the resilient characteristics of the spring steel enable the dental ring 100 to be slightly expanded by the use of, for example, manual forceps. The expanded dental ring 100 can then be placed around a tooth 124 that is adjacent to the decayed tooth 114 as best shown in FIG. 16. Thereafter, the pair of downward extending parallel flanges, i.e., the first parallel flange 108 and the second parallel flange 110, can be utilized to apply adequate force for slightly separating the adjacent tooth 124 from the decayed tooth 114 to provide access to an area of tooth decay.

As is clearly shown in FIG. 2, the first parallel flange 108 is slightly longer than the second parallel flange 110. The difference in the lengths of the pair of downward extending parallel flanges 108 and 110 is intended to facilitate the position of the protuberance 104 as will now be discussed. Each of the downward extending parallel flanges 108 and 110 includes an interior surface 106 as is shown in FIGS. 1 and 2. Since the protuberance 104 is also comprised of spring loaded steel, the protuberance 104 can be formed directly onto the interior surface 106 of, for example, the first parallel flange 108 during the manufacturing process as is clearly shown in FIG. 2. The protuberance 104 is formed onto the dental ring 100 so that it is preferably orthogonal (i.e., at right angles) to the interior surface 106 of the first vertical flange 108. As a general rule, the protuberance 104 formed onto the interior surface 106 at right angles provides the best performance. However, it is to be understood that a protuberance 104 formed at an angle other than ninety degrees could also function adequately within limitations.

In accordance with the preferred embodiment, the protuberance 104 is wedge-shaped as shown in FIGS. 1–5, and 17. However, it is noted that the protuberance 104 can also be cone-shaped, triangular-shaped, or even semi-circular-shaped. Therefore, in the preferred embodiment, the protuberance 104 is a wedge that includes a tip 126 as is clearly shown in FIG. 2. The tip 126 of the wedge protuberance 104 is shown positioned underneath the second parallel flange 110 in FIGS. 1, 2 and 4. Thus, the tip 126 of the wedge protuberance 104 can be extended into a triangular-shaped embrasure 128 (i.e., a triangular-shaped opening between the adjacent tooth 124 and the decayed tooth 114 shown in FIGS. 16 and 17) without interference from the second parallel flange 110. This design assures ease of manipulation of the dental ring 100 on the patient's teeth 102. The dental ring 100 facilitates the elimination of a component (i.e., a small wooden wedge) typically used in prior art dental rings. Consequently, the dental ring 100 of the present invention results in a more efficient and useful construction.

The procedure utilized when restoring the decayed tooth 114 when employing the dental ring 100 of the present invention includes the step of initially numbing the appropriate nerves in the area of the decayed tooth 114. Next, the decayed area of the decayed tooth 114 is removed by utilizing an appropriate drilling device for creating a box shaped receptacle for receiving dental filling material. The filling site is then prepared with the proper chemicals. Next, the concave matrix foil 112 is positioned between the adjacent tooth 124 and the decayed tooth 114 which is to be restored. The inventive dental ring 100 is then expanded with a pair of manual forceps (not shown) and positioned around the adjacent tooth 124. Simultaneously, the wedge-shaped orthogonal protuberance 104 is directed into the triangular-shaped embrasure 128 between the adjacent tooth 124 and the decayed tooth 114. As a result of this procedure, the protuberance 104 (a) forces the matrix foil 112 to wrap about the decayed tooth 114, (b) closes any slight space between the matrix foil 112 and the decayed tooth 114, (c) assists the dental ring 100 in grasping the undercut of the adjacent tooth 124 upon which it is mounted, and (d) prevents the dental ring 100 from "popping off" of the adjacent tooth 124 and into the mouth of the patient.

A first alternative embodiment of the dental ring for use in installing interproximal fillings in teeth and having a left-handed protuberance formed thereon is shown in FIGS. 6–10 and is referred to by the identification number 200. Each of the components appearing in the first alternative embodiment 200 that correspond in structure and function to those components appearing in the preferred embodiment 100 is identified by the corresponding number of the 200 series.

The components appearing in the first alternative embodiment of the dental ring 200 for use in installing interproximal fillings that correspond in structure and function to those components appearing in the preferred embodiment are set forth at this time. Those components include a left-handed protuberance 204 orthogonally formed onto an interior surface 206 of one of a pair of downward extending parallel flanges 208 and 210 shown best in FIGS. 6 and 7. The dental ring 200 also includes a circular ring 216 clearly shown in FIG. 6. The circular ring 216 includes a gap 218 which defines a first terminal end 220 and a second terminal end 222. The first parallel flange 208 extends from the first terminal end 220 while the second parallel flange 210 extends from the second terminal end 222. Additionally, each of the pair of downward extending parallel flanges 208 and 210 is positioned orthogonal to the plane of the circular ring 216. The pair of downward extending parallel flanges 208 and 210, the protuberance 204 formed on the interior surface 206 of one of the parallel flanges 208, 210, and the circular ring 216 including the first terminal end 220 and second terminal end 222, are each formed from spring loaded steel as previously described.

Figure 17:
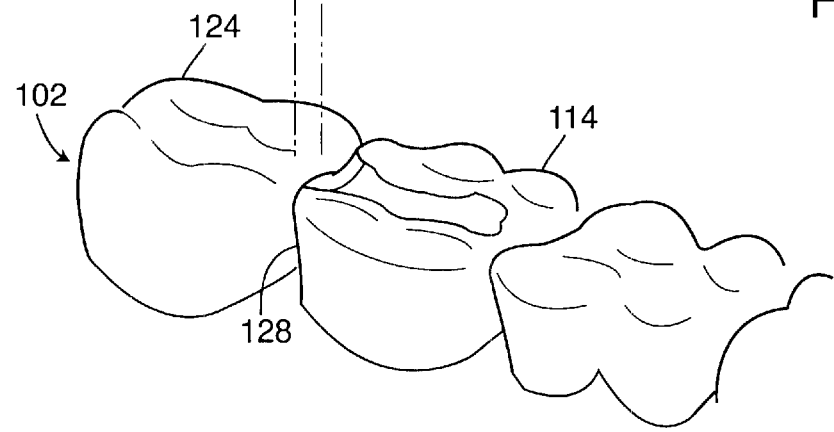
FIG. 17 is an exploded view of the dental ring of FIGS. 1 and 2 shown positioned above the tooth to be restored and including the inventive dental ring having at least one orthogonal protuberance and a matrix foil.

Certain components and structural features of the patient's dental anatomy are obviously the same in the dental ring 200 as they were in the preferred embodiment of the dental ring 100. These features are shown in FIGS. 16 and 17 as disclosed in the description of the dental ring 100. Consequently, these features are identical to those described in the preferred embodiment 100 and thus retain the corresponding identification number of the one-hundred series. These features include the teeth of the human patient 102, matrix foil 112, decayed tooth 114, adjacent tooth 124, and the embrasure 128 located between the adjacent tooth 124 and the decayed tooth 114, all shown in FIGS. 16 and 17. The teeth of the human patient 102, decayed tooth 114, adjacent tooth 124, and the embrasure 128 are each features or characteristics of the patient's dental anatomy. The matrix foil 112 is the thin contoured piece of aluminum metal having a concave shape that is placed between the adjacent tooth 124 and the decayed tooth 114 for retaining the filling material inserted into the decayed tooth 114.

The construction of the first alternative embodiment of the dental ring 200 to this point in the description is essentially identical to the construction of the dental ring 100 of the preferred embodiment. However, the distinguishing features of the dental ring 200 will now be disclosed. In the dental ring 200, the second parallel flange 210 is longer than the first parallel flange 208 as is clearly shown in FIG. 7. This condition is exactly opposite to that described in the preferred embodiment of the dental ring 100. Furthermore, the protuberance 204 is clearly shown as being formed onto the interior surface 206 of the second parallel flange 210 as is best shown in FIGS. 6 and 7. In the dental ring 200, the left-handed protuberance 204 is wedge-shaped as is clearly shown in FIG. 7 and is preferably orthogonally (i.e., at a right angle) formed onto the interior surface 206 of the second parallel flange 210. However, it is to be understood that the protuberance 204 can also be triangular-shaped, cone-shaped, or even semi-circular-shaped. As a general rule, the protuberance 204 formed onto the interior surface 206 at a right angle provides the best performance. However, it is to be understood that a protuberance 204 formed at an angle other than ninety degrees could also function adequately within limitations.

The wedge-shaped protuberance 204 includes a tip 226 as is clearly shown in FIG. 7. The tip 226 of the wedge protuberance 204 is shown positioned underneath the first parallel flange 208 in FIGS. 6, 7 and 9. Thus, the tip 226 of the wedge protuberance 204 can be extended into a triangular-shaped embrasure 128 (i.e., a triangular-shaped opening between the adjacent tooth 124 and the decayed tooth 114 shown in FIGS. 16 and 17) without interference from the first parallel flange 208 during placement of the dental ring 200 onto the adjacent tooth 124 for securing the matrix foil 112 into position. This design assures ease of manipulation of the dental ring 200 onto the patient's teeth 102. The dental ring 200 facilitates the elimination of a component (i.e., a small wooden wedge) typically used in prior art dental rings. Consequently, the dental ring 200 of the present invention results in a more efficient and useful construction.

The determination as to whether to utilize the dental ring 100 having the right-handed protuberance 104 or the dental ring 200 having the left-handed protuberance 204 depends upon several variables. Those variables include the anatomy of the patient's teeth 102, the rotation of the patient's teeth 102, the location of the cavity in the decayed tooth 114, and also the ease by which the selected dental ring can be positioned onto the adjacent tooth 124 during the interproximal filling procedure. The determination of which embodiment of the dental ring is selected is determined by which embodiment facilitates the placing of the filling material and restoring the contact between the teeth without the dental ring interfering with that procedure. Consequently, a plurality of embodiments of the dental ring are necessary such as, for example, in a set of dental rings, to accomplish this goal.

A second alternative embodiment of the dental ring for use in installing interproximal fillings in teeth and having both a right-handed protuberance and a left-handed protuberance formed thereon is shown in FIGS. 11–15 and is referred to by the identification number 300. Each of the components appearing in the second alternative embodiment 300 that correspond in structure and function to those components appearing in the preferred embodiment 100 is identified by the corresponding number of the 300 series.

The components appearing in the second alternative embodiment of the dental ring 300 for use in installing interproximal fillings that correspond in structure and function to those components appearing in the preferred embodiment are set forth at this time. Those components include a pair of downward extending parallel flanges 308 and 310 shown best in FIGS. 11 and 12 and a circular ring 316 clearly shown in FIG. 11. The circular ring 316 includes a gap 318 which defines a first terminal end 320 and a second terminal end 322. The first parallel flange 308 extends from the first terminal end 320 while the second parallel flange 310 extends from the second terminal end 322. Additionally, each of the pair of downward extending parallel flanges 308 and 310 is positioned orthogonal to the plane of the circular ring 316. The pair of downward extending parallel flanges 308 and 310, and the circular ring 316 including the first terminal end 320 and second terminal end 322, are each formed from spring loaded steel as previously described.

Certain components and structural features of the patient's dental anatomy are obviously the same in the dental ring 300 as they were in the preferred embodiment of the dental ring 100 and in the dental ring 200. These features are shown in FIGS. 16 and 17 as disclosed in the description of the dental ring 100. Consequently, these features are identical to those described in the preferred embodiment 100 and thus retain the corresponding identification number of the one-hundred series. These features include the teeth of the human patient 102, matrix foil 112, decayed tooth 114, adjacent tooth 124, and the embrasure 128 located between the adjacent tooth 124 and the decayed tooth 114, all shown in FIGS. 16 and 17. The teeth of the human patient 102, decayed tooth 114, adjacent tooth 124, and the embrasure 128 are each features or characteristics of the patient's dental anatomy. The matrix foil 112 is the thin contoured piece of aluminum metal having a concave shape that is placed between the adjacent tooth 124 and the decayed tooth 114 for retaining the filling material inserted into the decayed tooth 114.

Figure 11:
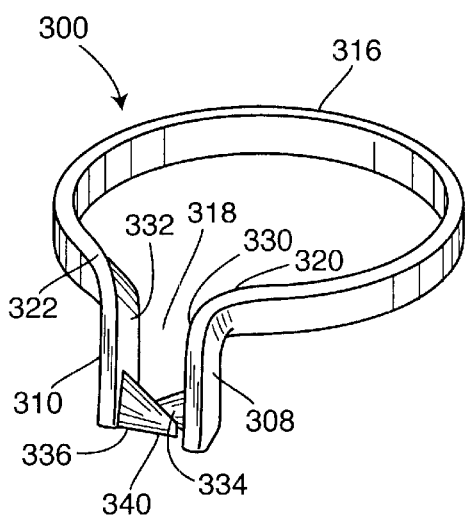
FIG. 11 is a perspective view of a second alternative embodiment of a dental ring of the present invention having both a right side orthogonal protuberance and a left side orthogonal protuberance and showing a pair of opposing offset wedges.
Figure 12:
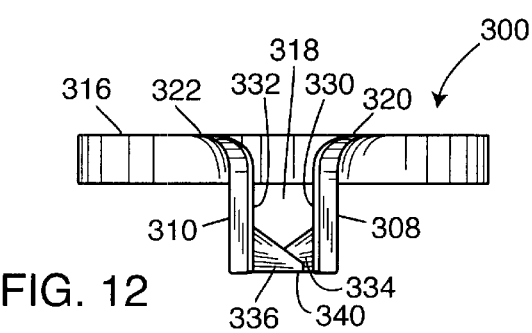
FIG. 12 is a front elevation of the dental ring of FIG. 11 showing the pair of opposing offset wedges each protruding from a corresponding one of a pair of downward extending parallel flanges.

The construction of the second alternative embodiment of the dental ring 300 to this point in the description is essentially identical to the construction of the dental ring 100 of the preferred embodiment. However, the distinguishing features of the dental ring 300 will now be disclosed. In the dental ring 300, the first parallel flange 308 and the second parallel flange 310 are of the same length as is clearly shown in FIGS. 11 and 12. This condition is distinguishable from that described in the dental ring 100 and the dental ring 200 wherein one of the pair of parallel flanges is longer than the other. Further, the first parallel flange 308 includes a first interior surface 330 and the second parallel flange 310 includes a second interior surface 332 as shown in FIGS. 11 and 12. Additionally, the dental ring 300 includes a right-handed protuberance 334 and a left-handed protuberance 336 also shown in FIG. 12. The right-handed protuberance 334 is clearly shown as being formed onto the first interior surface 330 of the first parallel flange 308 as is best shown in FIGS. 11 and 12. Likewise, the left-handed protuberance 336 is clearly shown as being formed onto the second interior surface 332 of the second parallel flange 310 also shown in FIGS. 11 and 12.

In the dental ring 300, both the right-handed protuberance 334 and the left-handed protuberance 336 are wedge-shaped as is clearly shown in FIG. 12. However, it is to be understood that the right-handed protuberance 334 and the left-handed protuberance 336 each can also be both triangular-shaped, or both cone-shaped, or even both semi-circular-shaped. Further, it is preferable that the right-handed protuberance 334 be orthogonally (i.e., at right angles) formed onto the first interior surface 330 of the first parallel flange 308. Likewise, it is preferable that the left-handed protuberance 336 be orthogonally (i.e., at right angles) formed onto the second interior surface 332 of the second parallel flange 310 as is shown in FIGS. 11 and 12. As a general rule, the right-handed protuberance 334 formed onto the first interior surface 330 at a right angle, and the left-handed protuberance 336 formed onto the second interior surface 332 at a right angle provides the best performance. However, it is to be understood that the right-handed protuberance 334 and the left-handed protuberance 336 when formed onto the first interior surface 330 and the second interior surface 332, respectively, at an angle other than ninety degrees could also function adequately within limitations.

Figure 13:
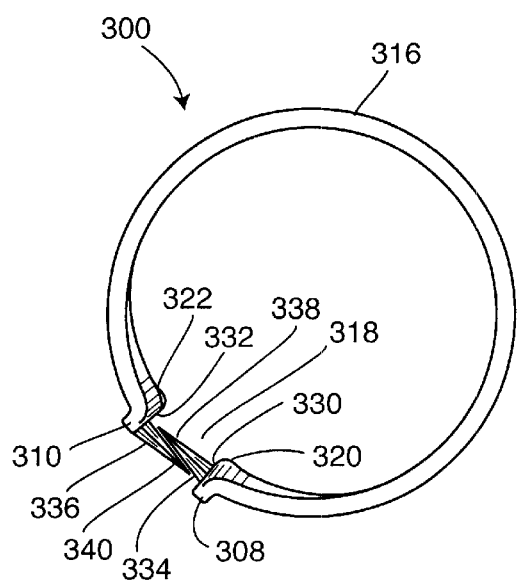
FIG. 13 is a top plan view of the dental ring of FIG. 11 showing a tip of each of the opposing offset wedges protruding from the corresponding pair of downward extending parallel flanges.
Figure 14:
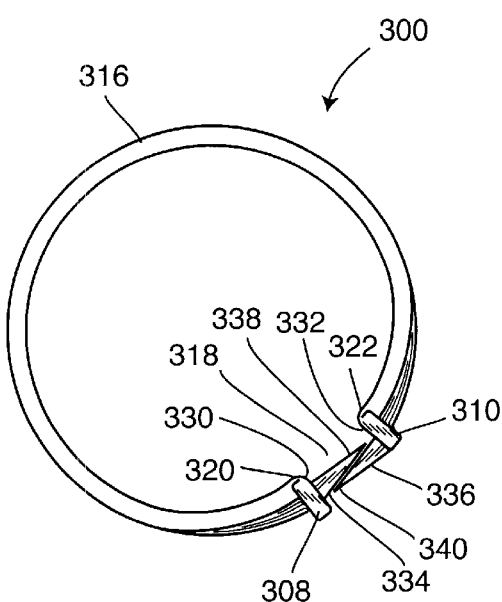
FIG. 14 is a bottom plan view of the dental ring of FIG. 11 showing the tips of the pair of opposing offset wedges protruding from the corresponding pair of downward extending parallel flanges.
Figure 15:
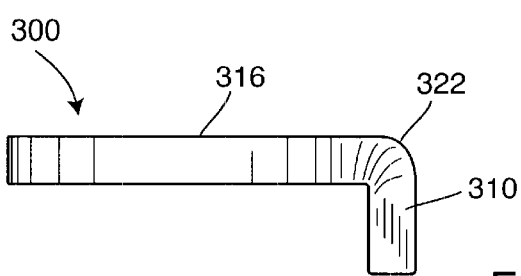
FIG. 15 is a side elevation of the dental ring of FIG. 11 showing the left downward extending parallel flange of the pair of downward extending parallel flanges.

The wedge-shaped, right-handed protuberance 334 includes a first tip 338 as is clearly shown in FIG. 13. Likewise, the wedge-shaped, left-handed protuberance 336 includes a second tip 340 also shown in FIG. 13. The first tip 338 of the right-handed protuberance 334 is shown positioned adjacent to the second tip 340 of the left-handed protuberance 336 in FIGS. 13 and 14. Thus, the first tip 338 of the right-handed protuberance 334 can be extended into a triangular-shaped embrasure 128 (i.e., a triangular-shaped opening between the adjacent tooth 124 and the decayed tooth 114 shown in FIGS. 16 and 17) during placement of the dental ring 300 onto the adjacent tooth 124 for securing the matrix foil 112 into position. Likewise, the second tip 340 of the left-handed protuberance 336 can also be extended into the triangular-shaped embrasure 128 (shown in FIGS. 16 and 17) during placement of the dental ring 300 onto the adjacent tooth 124 for securing the matrix foil 112 into position. This design assures ease of manipulation of the dental ring 300 onto the patient's teeth 102. The dental ring 300 facilitates the elimination of a component (i.e., a small wooden wedge) typically used in prior art dental rings. Consequently, the dental ring 300 of the present invention results in a more efficient and useful construction.

The determination as to when the dental ring 300 having the right-handed protuberance 334 and the left protuberance 336 would be utilized for securing the matrix foil 112 about the decayed tooth 114 depends upon the same variables as for the dental ring 100 having the right-handed protuberance 104 or the dental ring 200 having the left-handed protuberance 204. ** Those variables include the anatomy of the patient's teeth 102, the rotation of the patient's teeth 102, the location of the cavity in the decayed tooth 114, and also the ease by which the selected dental ring can be positioned onto the adjacent tooth 124 during the interproximal filling procedure. The determination of which embodiment of the dental ring is selected is determined by which embodiment facilitates the placing of the filling material and the restoring of the contact between the teeth without the dental ring interfering with that procedure. Consequently, a plurality of embodiments of the dental ring are necessary such as, for example, in a set of dental rings, to accomplish this goal. Under these conditions, the most suitable dental ring can be utilized.

The present invention provides novel advantages over other conventional dental rings for use in installing interproximal fillings in human teeth. A main advantage includes orthogonally forming a protuberance 104 comprised of spring loaded material onto an interior surface 106 of one of the downward extending parallel flanges 108 or 110 for securing a matrix foil 112 about a decayed tooth 114. The dental ring 100 facilitates the elimination of a component (i.e., a small wooden wedge) typically used in prior art dental rings. Consequently, the dental ring 100 of the present invention results in a more efficient and useful construction. A further advantage is that the protuberance 104 formed onto the interior surface 106 of one of the pair of parallel flanges 108 or 110 can be wedge-shaped, cone-shaped, triangular-shaped or even semi-circular-shaped.

Additionally, the dental ring 100 can be fabricated so that one of the pair of downward extending parallel flanges 108 or 110 is longer than the other. This design enables the protuberance 104 to be formed onto the longer of the parallel flanges 108, 110 thus avoiding interference between the protuberance 104 and the shorter of the parallel flanges 108 or 110. Additionally, when the protuberance 104 is extended into the embrasure between two teeth 102, the matrix foil 112 is forced to wrap around the decayed tooth 114, the space between the matrix foil 112 and the decayed tooth 114 is closed, the dental ring 100 can more easily grasp the undercut of the decayed tooth 114, and the protuberance 104 prevents the dental ring 100 from "popping off" into the patient's mouth. In another embodiment, each of the pair of parallel flanges includes a separate protuberance for facilitating the adherence of the matrix foil about the decayed tooth 114.

While the present invention is described herein with reference to illustrative embodiments for particular applications, it should be understood that the invention is not limited thereto. Those having ordinary skill in the art and access to the teachings provided herein will recognize additional modifications, applications and embodiments within the scope thereof and additional fields in which the present invention would be of significant utility.

It is therefore intended by the appended claims to cover any and all such modifications, applications and embodiments within the scope of the present invention. Accordingly,

What is claimed is:

1. A dental ring for use in installing interproximal fillings in teeth comprising:

a circular ring comprised of metal and including a gap formed in said ring for defining a first terminal end and a second terminal end;

a pair of downward extending parallel flanges including a first parallel flange extending from said first terminal end and a second parallel flange extending from said second terminal end, said parallel flanges for separating a decayed tooth from an adjacent tooth, and said first parallel flange being longer than said second parallel flange; and a protuberance formed onto an interior surface of said first parallel flange for securing a matrix foil about said decayed tooth.

2. The dental ring of claim 1 wherein said circular ring is comprised of spring steel.

3. The dental ring of claim 1 wherein said protuberance is wedge-shaped.

4. The dental ring of claim 1 wherein said protuberance is comprised of steel.

5. The dental ring of claim 1 wherein said protuberance is orthogonally formed onto said interior surface of said first parallel flange.

6. A dental ring for use in installing interproximal fillings in teeth comprising:

a circular ring comprised of metal and including a gap formed in said ring for defining a first terminal end and a second terminal end;

a pair of downward extending parallel flanges including a first parallel flange extending from said first terminal end and a second parallel flange extending from said second terminal end, said parallel flanges for separating a decayed tooth from an adjacent tooth, and said second parallel flange being longer than said first parallel flange; and a protuberance formed onto an interior surface of said second parallel flange for securing a matrix foil about said decayed tooth.

7. The dental ring of claim 6 wherein said circular ring and said protuberance are each comprised of spring steel.

8. The dental ring of claim 6 wherein said protuberance is wedge-shaped.

9. The dental ring of claim 6 wherein said protuberance is orthogonally formed onto said interior surface of said second parallel flange.

* * * * *